United States Patent [19]

Eisele

[11] Patent Number: 5,067,496
[45] Date of Patent: Nov. 26, 1991

[54] TRACHEOSTOMY TUBE

[75] Inventor: Robert F. Eisele, Laguna Niguel, Calif.

[73] Assignee: Shiley Incorporated, Irvine, Calif.

[21] Appl. No.: 178,661

[22] Filed: Apr. 7, 1988

[51] Int. Cl.$^5$ .......................................... A61M 16/00
[52] U.S. Cl. ........................... 128/207.15; 128/207.14
[58] Field of Search ....................... 128/207.14, 207.15

[56] References Cited

U.S. PATENT DOCUMENTS 4,315,505  2/1982  Crandall et al. ............... 128/207.15

Primary Examiner—Edgar S. Burr
Assistant Examiner—Aaron J. Lewis
Attorney, Agent, or Firm—P. C. Richardson; L. C. Akers; R. C. Turner

[57] ABSTRACT

The specification discloses a tracheostomy tube which includes an outer cannula which has a tubular wall, a distal end for placement within the trachea of a patient and a proximal end for placement outside of the trachea. The outer cannula has an inflatable cuff attached near the distal end thereof for forming a seal with the tracheal wall. A flexible inflation tube extends from within the cuff and has a portion fixedly secured along the wall of the outer cannula to a point that is near, but not at, the proximal end of the outer cannula and further extends unsecured. An annular retaining collar, has a flange with an aperture in longitudinal alignment with the secured portion and which is adapted to receive the inflation tube, and is attached to the proximal end of the outer cannula. The unsecured inflation line is routed through the aperture and is thereby retained by the flange in the collar, whereby any force on the unsecured inflation tube proximal of the collar results in substantially only tensile forces being exerted on the junction of the unsecured portion and the fixedly secured portion of the inflation tube.

13 Claims, 1 Drawing Sheet

TRACHEOSTOMY TUBE

BACKGROUND OF THE INVENTION

The present invention relates to a tracheostomy tube particularly a tracheostomy tube having an inflation tube for inflating a cuff for forming a seal with the tracheal wall of a patient.

Tracheostomy tubes have been used for some time to provide a bypass supply of air or mixture of gases to a patient having an obstruction in the larynx or the pharynx area of the throat. The distal end of an outer cannula is inserted into the trachea through an incision in the patient's neck below the obstructed area. The proximal end of the outer cannula remains outside the trachea in communication with ambient air to permit passage of such air into the trachea. U.S. Pat. No. 3,693,624, also assigned to the assignee of the present invention, discloses a tracheostomy tube having an inner cannula which serves as an inner liner of the outer cannula and can be removed, cleaned, and then replaced. The proximal end of the tube can also be attached to a respiratory device to assist the patient's breathing. The distal end also includes an inflatable cuff to seal the distal end of the outer cannula within the tracheal wall to further assist the patient's breathing on the respiratory device, as described in U.S. Pat. No. 3,659,612 assigned to the assignee of the present invention and incorporated herein by reference.

The cuff is inflated and deflated by a small, flexible inflation tube and has a small valve at the proximal end of the inflation tube. The inflation tube has one end sealed within the cuff and is further fixedly bonded within a recess which extends from the cuff to the proximal end along the lower wall portion of the outer cannula. The remainder of the inflation tube extends unsecured and generally perpendicularly away from the proximal end of the outer cannula.

The unsecured portion of the inflation tube is subjected to various forces during inflation, deflation and normal handling while in use. In some (about 1 percent) of the tracheostomy tubes of the prior art, after only a few weeks of use, the inflation tube breaks at the point where it was fixedly bonded at the proximal end of the outer cannula. When the inflation tube breaks, the cuff deflates and cannot be resealed within the tracheal wall. The tracheostomy tube must then be replaced for patients requiring ventilation, at considerable inconvenience and expense.

SUMMARY OF THE INVENTION

It is an object of the present invention to provide a durable, dependable inflation tube which does not break from a cuffed tracheostomy tube.

It is another object of the present invention to provide a durable, dependable inflation tube for a cuffed tracheostomy tube which can be readily retrofit to components in inventory and readily adapted to current tooling.

The present invention solves the breakage problem and meets the objectives by providing an improved tracheostomy tube in which a cuff inflation tube is uniquely secured to and retained by the tracheostomy tube. The tracheostomy tube includes an outer cannula which has a tubular wall, a distal end for placement within the trachea of a patient and a proximal end for placement outside of the trachea. The outer cannula has an inflatable cuff attached near the distal end thereof for forming a seal with the tracheal wall. A flexible inflation tube extends from within the cuff and has a portion fixedly secured along the wall of the outer cannula to a point that is near, but not at, the proximal end of the outer cannula and further extends unsecured. An annular retaining collar, has a flange with an aperture in longitudinal alignment with the secured portion and which is adapted to receive the inflation tube, and is attached to the proximal end of the outer cannula. The unsecured inflation line is routed through the aperture and is thereby retained by the flange in the collar, whereby any force on the unsecured inflation tube proximal of the collar results in substantially only tensile forces being exerted on the junction of the unsecured portion and the fixedly secured portion of the inflation tube. It has been determined that the junction of the unsecured portion and the fixedly secured portion of the inflation tube has very little lateral shear strength but has significantly higher tensile strength. Therefore, the inflation tube retaining collar of the present inventions translates any forces into tensile stresses and allows the inflation tube to withstand repeated relatively large forces without failure.

BRIEF DESCRIPTION OF THE DRAWINGS

While the novel features of the invention are set forth with particularity in the appended claims, the invention will be better understood along with other features thereof from the following detailed description taken in conjunction with the drawings, in which:

DETAILED DESCRIPTION OF THE INVENTION

Figure 1:
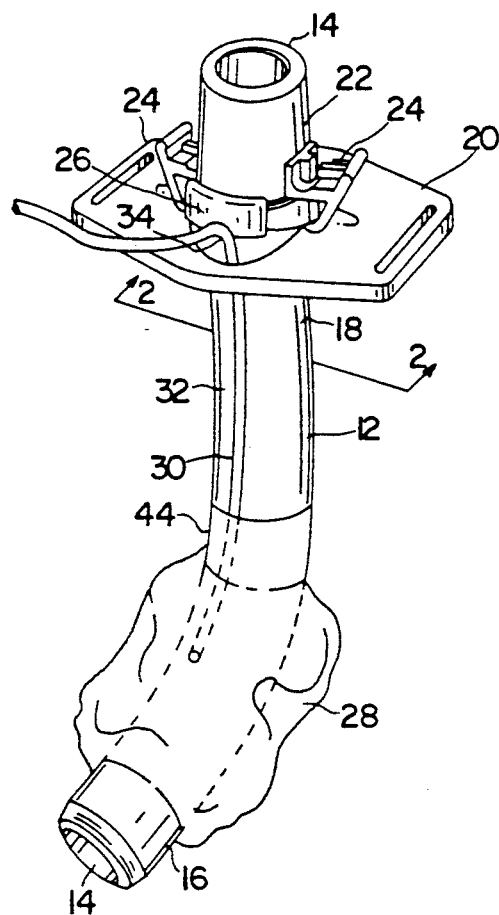
FIG. 1 is a bottom front perspective view of a typical cuffed tracheostomy tube of the prior art.
Figure 2:
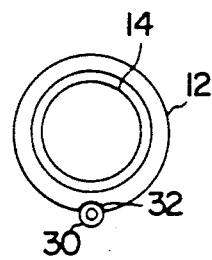
FIG. 2 is a sectional view taken along line 2—2 of FIG. 1.

Referring initially to FIGS. 1 and 2, there is shown a tracheostomy tube 10 of the prior art, including an outer cannula 12, and a removable inner cannula 14. The outer cannula is comprised of a tube having a circular longitudinal radius of curvature, a distal end 16 for insertion into the trachea of the patient through an opening in the neck and a proximal end 18 remaining outside the trachea. A typical outer cannula is manufactured from semi-rigid polyvinyl chloride (PVC) and has a central radius of curvature of about 2.20 inches, an arcuate length of about 85 degrees and a wall thickness of about 0.060 inches. A swivel neck flange 20 located near the proximal end 18 of the outer cannula is used to secure the tracheostomy tube 10 through the neck of the patient. The inner cannula 14 is fully inserted into the outer cannula and is secured by a coupling connector 22 having suitable arms 24 which engage an annular collar 26 (of the prior art) which is attached at the proximal end 18 of the outer cannula. Shown attached to the tracheostomy tube 10 near its distal end 16 is an inflatable cuff 28, which, when inflated, provides an air-tight seal between the tracheostomy tube and the inner wall of the trachea. Such sealing cuffs are described in more detail in U.S. Pat. No. 3,659,612 and U.S. Pat. No. 3,693,624, assigned to Shiley Inc. The cuff 28 is inflated by means of a pressurization valve (not shown) connected to a flexible inflation tube 30 which is sealed within the cuff 28. A suitable inflation tube is formed of flexible PVC and has an outer diameter of about 0.060 inches and and inner diameter of about 0.030 inches, and extends about 12 inches from the proximal end of the tracheostomy tube for easy access for inflation.

The inflation tube 30 is secured within a longitudinal recess 32 (see FIG. 2) which is formed into the lower surface of the wall of the outer cannula 12. The recess 32 is adapted to confine the inflation tube 30 with a smooth outer surface contour and is about 0.060 inches wide and about 0.050 inches deep with a semi-cylindrical bottom. The recess 32 originates on the outer cannula at a location within the cuff 28 and extends along the outer surface and terminates in the annular collar 26 at the proximal end of the outer cannula. The PVC inflation tube is positioned in the recess 32 and fixedly bonded over the entire length of the recess (in the prior art) by a lacquer solution of 6 percent PVC dissolved in cyclohexanon. The inflation tube 30 exits the recess generally perpendicularly at the retainer collar 26 and extends unsupported downwardly about 12 inches to the pressurization valve where it can be inflated and deflated with a hypodermic type plunger device. The inflation tube is thereby fixedly bonded to the outer cannula at junction 34, which is the junction of the secured portion and the unsecured portion and which is the common location where the inflation tube would often break from the tracheostomy tubes. The material of the cannulae and many of the failed inflation tubes were chemically analyzed and a variety of different materials, glues, and epoxies were tried in attempts to bond the inflation tube to the outer cannula in a manner so that the inflation tube would not break. As a result of the analysis of the testing, it was concluded that the failures were not due to chemical reactions of the various materials and solvent bonds; but were due to a stress concentration which is created at the junction 34 of the fixedly bonded portion and the unsecured portion of the inflation tube. It was determined that the junction would fail under small lateral shear forces (of about 5 pounds) but could withstand substantially higher longitudinal tensile forces (of about 10 pounds) at the junction. However, since the inflation tube 30 extends generally perpendicularly downwardly from the proximal end of the outer cannula, nearly any force exerted on the inflation tube results in significant shear forces at the junction 34 which corresponds to the failures of the inflation tube at that point.

Figure 3:
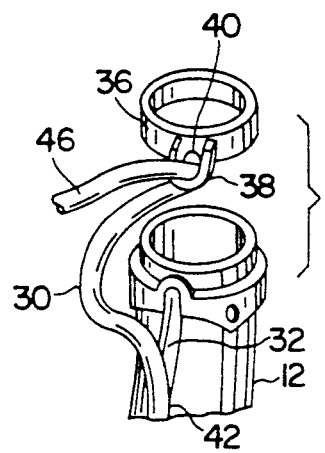
FIG. 3 is a bottom front perspective, exploded partial view of a cuffed tracheostomy tube having the annular retaining collar of the present invention.

Referring now also to FIG. 3 the present invention is illustrated which solves the breakage problem of the inflation tube 30. The invention preferable includes a typical neck flange (20) which is not shown (in FIGS. 3, 4, and 5) so that the invention is more clearly illustrated. The inflation tube 30 is secured to the outer cannula so that the junction between the fixedly secured portion and the unsecured portion of the inflation tube is protected from lateral shear forces. This is accomplished by an annular retaining collar 36. The annular retaining collar 36 includes a flange 38 which extends generally parallel with the outer cannula which has an aperture 40 which is sized to closely surround the diameter of the inflation tube 30. The annular retaining collar 36 is adapted to be attached to the outer cannula so that the aperture 40 in flange 38 is in precise alignment with longitudinal recess 32. In addition, the inflation tube 30 is bonded into recess 32 from the cuff 28 along the outer cannula only to a point shown as (junction) bonding point 42 which is approximately 0.25 inches in the distal direction from the aperture 40 in flange 38. This leaves about 0.25 inches of unsecured longitudinally aligned inflation tube between the bonding point 42 and the retaining collar 36.

The manufacturing process resulting in the improved retention of the inflation tube involves first, the placement of the distal end of the inflation tube 30 in the desired position within recess 32, the inflation tube is then bonded with the lacquer solution from its distal end along the recess of the outer cannula to the bonding point 42 near (spaced about 0.25 inches from) the proximal end of the outer cannula; the distal end of the inflatable cuff 28 is then sealed over the distal end of the outer cannula and the proximal end 44 of the cuff is sealed over the outer cannula 12 and the inflation tube 30. The unsecured portion of the inflation line 30 is then routed through aperture 40 of flange 38 and the annular retaining collar 36 is attached to the distal end 18 of the outer cannula 12. The neck flange and inner cannula are installed to complete the assembly. It is readily seen, that any force exerted in any direction on the unsecured portion 46 of the inflation tube will be translated by the flange 38 into an axial longitudinal tensile stress on any portion of the inflation tube which is proximal of flange 38. This is particularly significant for the bonding point 42 which is proximal of the flange 39 and which is now the junction (and stress concentration) between the fixedly bonded and the unsecured portion of the inflation tube. The flexible inflation tube 30 generally bends and flexes around the aperture 40 in flange 38 free of any stress concentration, and any forces are generally distributed over a relatively large area.

It was found that the inflation line 30 retained and secured in the configuration of the present invention withstands approximately twice the perpendicularly applied lateral force (about 8-10 pounds) on the unsecured portion 46 compared to the applied lateral force (about 5 pounds) required to break the inflation line from the configuration of the prior art. More significantly, a comparison fatigue test was conducted in which a one pound force was applied to the end of the unsecured inflation tube 46, and the inflation tube was cycled laterally from side to side through a 180° arc. The prior art configuration typically failed prior to 500 cycles. Each of the test samples of the configuration of the present invention successfully completed 5000 cycles without failure; and the samples which were tested to failure all exceeded 50,000 cycles. It is concluded that the present invention solves the breakage problem.

Figure 4:
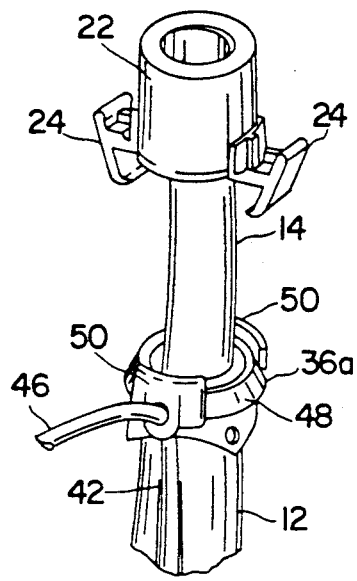
FIG. 4 is a bottom front perspective partial view of a particular configuration of the present invention.

Referring to FIG. 4, there is shown a specific configuration of an annular retaining collar 36a. Annular retaining collar 36a is particularly adapted to receive the disposable inner cannula 14 as discussed in reference to the prior art. The retaining collar 36a further includes a distal facing flange 48 with a tapered outer surface adapted to be engaged by retaining arms 24 to secure the inner cannula 14 within the outer cannula 12. The retaining collar 36a also includes a pair of tabs 50 which prevent rotation of the inner cannula by restricting rotational movement of the retaining arms 24. Retaining collar 36a is securely attached to the outer cannula 12 and further illustrates that any force on the unsecured portion 46 would be transferred by the retaining collar into an axial longitudinal tensile stress at the bonding point 42, substantially free of any lateral shear stresses, to improve the strength and endurance of the inflation tube 30.

Figure 5:
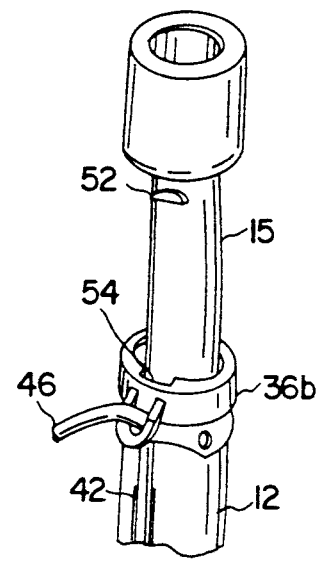
FIG. 5 is a front perspective partial view of another configuration of the present invention.

Referring to FIG. 5, there is illustrated another specific configuration of an annular retaining collar 36b. Retaining collar 36b is further adapted to receive an inner cannula known as the twist lock inner cannula 15. The twist lock inner cannula includes a pair of twist lock projections 52 at the proximal end thereof and the annular retaining collar 36b is adapted to receive the twist lock projections in a spiralled locking recess 54 (as described in detail in U.S. Pat. No. 3,659,612). The annular retaining collar 36b is otherwise similar to the retaining collar as described in reference to FIG. 3. Similarly, a force at the unsecured portion 46 would tend to produce only axial tensile stresses at bonding point 42 to thereby eliminate any lateral shear stresses which would tend to break the inflation tube 30 from the tracheostomy tube.

A variety of retaining means are possible in addition to those suggested by the annular retaining collar 36. A variety of retaining loops which are circular, oval, U-shaped, or horseshoe shaped could be attached to the proximal end of the outer cannula to generally surround and retain an unsecured portion of the inflation tube 30. Similarly, an inflation tube that is enclosed within the wall of the outer cannula is fixedly bonded only at the distal end such that the exit at the proximal end is unsecured and thereby transmits only tensile forces to the fixedly bonded portion.

The present invention provides a durable, dependable configuration for securing an inflation tube which does not break from a cuffed tracheostomy tube. The configuration requires the modification and retooling of only one component, the annular retaining collar, so the solution is quickly implemented and retrofit to known configurations of the prior art.

While specific embodiments of the present invention have been illustrated and described herein, it is realized that modifications and changes will occur to those skilled in the art. It is therefore to be understood that the appended claims are intended to cover all such modifications and changes as fall within the true spirit and scope of the invention.

What is claimed is:

1. A tracheostomy tube for insertion into the trachea of a patient to support breathing, comprising:
    An outer cannula having a distal end for placement within the trachea and a proximal end for placement outside of the trachea;
    a neck flange connected to the proximal end of said outer cannula for securing the tracheostomy tube to the patient;
    inflatable sealing means near the distal end of said outer cannula for forming a seal with the tracheal walls;
    a flexible inflation tube extending from within said sealing means and having a portion fixedly secured along the wall of said outer cannula near the proximal end of said outer cannula and said inflation tube further extending unsecured; and
    means retaining a portion of said unsecured inflation tube at the proximal end of said outer cannula in longitudinal alignment with said secured portion, whereby any pulling force on said inflation tube proximal of said retaining means results is substantially only tensile force on the secured portion of said inflation tube.

2. A tracheostomy tube as in claim 1 wherein said retaining means comprises a portion of a flange having an aperture longitudinally aligned with the secured portion and adapted to closely surround said inflation tube.

3. A tracheostomy tube as in claim 2 wherein said aperture is generally circular in shape.

4. A tracheostomy tube as in claim 2 wherein said aperture is generally semi-circular in shape.

5. A tracheostomy tube as in claim 2 wherein a portion of said flange extends generally parallel with said outer cannula whereby the aperture is generally perpendicular to the proximal end of said outer cannula.

6. A tracheostomy tube as in claim 1 wherein said retainer means comprises a generally annular collar having a flange with an aperture aligned with the secured portion and which is adapted to receive said inflation tube, and said collar is attached to the proximal end of said outer cannula.

7. A tracheostomy tube as in claim 6 wherein said collar is further adapted for securing an inner cannula within said outer cannula.

8. A tracheostomy tube for insertion into the trachea of a patient to support breathing, comprising:
    an outer cannula having a tubular wall, a distal end for placement within the trachea and a proximal end for placement outside of the trachea;
    a neck flange connected to the proximal end of said outer cannula for securing the tracheostomy tube to the patient;
    an inflatable sealing means near the distal end of said out cannula for forming a seal with the tracheal wall;
    a flexible inflation tube extending from within said sealing means;
    said outer cannula having a longitudinal recess in the wall thereof adapted to receive said inflation tube;
    said inflation tube fixedly secured within said recess near the proximal end of said outer cannula, and said tube further extending unsecured;
    an annular retaining collar adapted to substantially surround and align a portion of said unsecured inflation tube at the proximal end of said outer cannula, whereby any pulling force on said inflation tube proximal of said retaining collar results in substantially only tensile forces on the secured portion of said inflation tube.

9. A tracheostomy tube as in claim 8 wherein said annular retaining collar includes a flange with an aperture which is aligned with the recess in said outer cannula.

10. A tracheostomy tube as in claim 9 wherein said flange extends generally parallel with said outer cannula whereby the aperture is generally perpendicular to the proximal end of said outer cannula.

11. A tracheostomy tube as in claim 10 wherein said retaining collar is further adapted for securing an inner cannula within said outer cannula.

12. A tracheostomy tube as in claim 11 further comprising a twist-lock inner cannula and said retaining collar is adapted to engage and secure said inner cannula.

13. A tracheostomy tube as in claim 11 further comprising a disposable inner cannula having a pair of securing arms at the proximal end thereof, and said retaining collar includes a pair of distal facing shoulders adapted to engage and secure the arms of said disposable inner cannula.

* * * * *